United States Patent
Zhang et al.

(10) Patent No.: US 11,740,306 B2
(45) Date of Patent: Aug. 29, 2023

(54) SYSTEMS AND METHODS FOR MAGNETIC RESONANCE T1 MAPPING

(71) Applicant: SHANGHAI UNITED IMAGING HEALTHCARE CO., LTD., Shanghai (CN)

(72) Inventors: Zhongqi Zhang, Houston, TX (US); Yuan Zheng, Houston, TX (US); Jian Xu, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/456,890

(22) Filed: Nov. 30, 2021

(65) Prior Publication Data

US 2023/0168326 A1    Jun. 1, 2023

(51) Int. Cl.
*G01R 33/50* (2006.01)
*A61B 5/055* (2006.01)
*G06T 7/00* (2017.01)
*G01R 33/567* (2006.01)

(52) U.S. Cl.
CPC .............. *G01R 33/50* (2013.01); *A61B 5/055* (2013.01); *G01R 33/567* (2013.01); *G06T 7/0012* (2013.01); *G06T 2207/10088* (2013.01); *G06T 2207/20081* (2013.01)

(58) Field of Classification Search
CPC ...... G01R 33/50; G01R 33/567; A61B 5/055; G06T 7/0012; G06T 2207/10088; G06T 2207/20081
See application file for complete search history.

(56) References Cited

U.S. PATENT DOCUMENTS

| | | | |
|---|---|---|---|
| 9,008,753 B2 | 4/2015 | Messroghli | |
| 9,285,446 B2 | 3/2016 | Piechnik et al. | |
| 9,395,431 B2* | 7/2016 | Detsky | G01R 33/5614 |
| 9,791,532 B2* | 10/2017 | Greiser | G01R 33/5673 |
| 10,591,568 B2* | 3/2020 | Rehwald | G01R 33/56509 |
| 2012/0232378 A1* | 9/2012 | Messroghli | G01R 33/56325 |
| | | | 600/413 |
| 2013/0272591 A1* | 10/2013 | Xue | G06T 11/003 |
| | | | 382/131 |
| 2014/0200436 A1* | 7/2014 | Weingartner | G01R 33/5602 |
| | | | 600/413 |
| 2014/0314289 A1* | 10/2014 | Spottiswoode | G06T 7/0012 |
| | | | 382/128 |
| 2015/0099964 A1* | 4/2015 | Voigt | A61B 5/7282 |
| | | | 600/420 |
| 2015/0123659 A1* | 5/2015 | Weingartner | G01R 33/50 |
| | | | 324/309 |

(Continued)

FOREIGN PATENT DOCUMENTS

CN           11583356 A     8/2020

*Primary Examiner* — Dixomara Vargas
(74) *Attorney, Agent, or Firm* — METIS IP LLC

(57) ABSTRACT

The present disclosure provides systems and methods for MR T1 mapping. A method may include obtaining at least three images of a subject acquired within an inversion recovery (IR) process, each image of the at least three images being acquired within a cardiac cycle during a breath-hold of the subject; and determining a T1 map of the subject based on the at least three images acquired within the IR process and a trained model.

20 Claims, 9 Drawing Sheets

600

Obtaining at least three images of a subject acquired after the subject being applied an inversion recovery (IR) pulse, each image of the at least three images being acquired within a cardiac cycle during a breath-hold of the subject — 602

Determining a T1 map of the subject based on the at least three images acquired after the IR pulse and a trained model — 604

800

For an element location in a T1 map, determining a T1 value by inputting into the trained model at least three values of elements each of which is at a corresponding element location in one of the at least three images acquired within one IR process and an image acquisition time of each of the at least three images — 802

Determining the T1 map based on a plurality of T1 values of a plurality of element locations in the T1 map — 804

(56) References Cited

U.S. PATENT DOCUMENTS

| | | | |
|---|---|---|---|
| 2015/0323630 A1* | 11/2015 | Weingartner | G01R 33/543 |
| | | | 324/309 |
| 2017/0076449 A1* | 3/2017 | Chow | G06T 7/0012 |
| 2017/0219671 A1* | 8/2017 | Sugiura | G01R 33/50 |
| 2017/0307699 A1* | 10/2017 | Rodgers | G01R 33/56527 |
| 2018/0217217 A1* | 8/2018 | Weingartner | G01R 33/50 |
| 2018/0275235 A1* | 9/2018 | Reeder | G01R 33/543 |
| 2018/0292484 A1 | 10/2018 | Hoppe et al. | |
| 2018/0292503 A1* | 10/2018 | Slavin | G01R 33/50 |
| 2018/0306882 A1* | 10/2018 | Li | G06V 10/774 |
| 2019/0154785 A1* | 5/2019 | Zhou | A61B 5/055 |
| 2020/0375463 A1* | 12/2020 | Hess | A61B 5/0507 |
| 2021/0027436 A1 | 1/2021 | Banerjee et al. | |
| 2021/0325496 A1* | 10/2021 | Zheng | G01R 33/5619 |

* cited by examiner

600

Obtaining at least three images of a subject acquired after the subject being applied an inversion recovery (IR) pulse, each image of the at least three images being acquired within a cardiac cycle during a breath-hold of the subject — 602

Determining a T1 map of the subject based on the at least three images acquired after the IR pulse and a trained model — 604

800

802 — For an element location in a T1 map, determining a T1 value by inputting into the trained model at least three values of elements each of which is at a corresponding element location in one of the at least three images acquired within one IR process and an image acquisition time of each of the at least three images 804 — Determining the T1 map based on a plurality of T1 values of a plurality of element locations in the T1 map

902 — Obtaining a plurality of sample sets

904 — Obtaining the trained model by training a preliminary model based on the plurality of sample sets

FIG. 9

SYSTEMS AND METHODS FOR MAGNETIC RESONANCE T1 MAPPING

TECHNICAL FIELD

The present disclosure generally relates to magnetic resonance imaging (MRI), and more particularly, relates to systems and methods for MR T1 mapping.

BACKGROUND

In magnetic resonance imaging (MRI), a T1 value refers to a longitudinal (or spin-lattice) relaxation time of tissue. T1 mapping is used to calculate the T1 values of the tissue. Calculated T1 values may be displayed at element locations (e.g., pixel locations, voxel locations) on a parametric map (e.g., a T1 map). T1 mapping has been applied in clinical practice for disease diagnosis and risk stratification of myocardial tissue. Existing T1 mappings suffer from long scan time and low resolutions. For example, during a T1 mapping process using a Modified Look-Locker Inversion Recovery (MOLLI) algorithm, a patient usually needs to hold breath for eleven cardiac cycles to acquire eight images to calculate T1 values. And complicated calculations involved in processing such images usually result in inaccurate results. Therefore, it is desirable to provide systems and methods for MR T1 mapping with a short scan time and high accuracy.

SUMMARY

According to one aspect of the present disclosure, a system for MR T1 mapping is provided. The system may include at least one storage device including a set of instructions, and at least one processor configured to communicate with the at least one storage device. When executing the set of instructions, the at least one processor is directed to cause the system to perform operations including: obtaining at least three images of a subject acquired within an inversion recovery (IR) process, each image of the at least three images being acquired within a cardiac cycle during a breath-hold of the subject; and determining a T1 map of the subject based on the at least three images acquired within the IR process and a trained model.

In some embodiments, the operations further include: obtaining one or more processed images by processing one or more images of the at least three images; and determining the T1 map of the subject based on the one or more processed images and the trained model.

In some embodiments, the obtaining the one or more processed images by processing the one or more images of the at least three images includes: obtaining the one or more processed images by performing at least one of a motion correction algorithm or a phase correction algorithm on the one or more images of the at least three images.

In some embodiments, the trained model includes a fully connected neural network.

In some embodiments, the determining the T1 map of the subject based on the at least three images and the trained model includes: obtaining the T1 map of the subject by inputting the at least three images into the trained model, wherein the T1 map is an output of the trained model.

In some embodiments, the determining the T1 map of the subject based on the at least three images and the trained model includes: for an element location in the T1 map, determining a T1 value by inputting into the trained model at least three values of elements each of which is at a corresponding element location in one of the at least three images and an image acquisition time of each of the at least three images; and determining the T1 map based on a plurality of T1 values of a plurality of element locations in the T1 map.

In some embodiments, for an element location in the T1 map, the determining the T1 value includes: for each image of the at least three images, identifying an image acquisition time of the image, the image acquisition time being a time point at which the image is acquired during the IR process; and identifying a value of an element at each element location of the image.

In some embodiments, the trained model is determined based on a training process and the training process includes: obtaining a plurality of sample sets, wherein each sample set includes a plurality of sample images, a plurality of sample image acquisition times each of which corresponds to one of the plurality of sample images, and a reference T1 map of the plurality of sample images; and obtaining the trained model by training a preliminary model based on the plurality of sample sets In some embodiments, the obtaining the plurality of sample sets includes: for a sample set of the plurality of sample sets, obtaining the plurality of sample images; identifying a sample image acquisition time of each of the plurality of sample images; and determining the reference T1 map of the plurality of sample images based on the plurality of sample images and the corresponding sample image acquisition times.

In some embodiments, the plurality of sample images of a sample set are acquired using a Modified Look-Locker Inversion Recovery (MOLLI) sequence.

In some embodiments, the reference T1 map of the plurality of sample images is determined according to a fitting algorithm.

According to another aspect of the present disclosure, a method for MR T1 mapping is provided. The method may include: obtaining at least three images of a subject acquired within an inversion recovery (IR) process, each image of the at least three images being acquired within a cardiac cycle during a breath-hold of the subject; and determining a T1 map of the subject based on the at least three images acquired within the IR process and a trained model.

According another aspect of the present disclosure, a non-transitory readable medium including at least one set of instructions is provided. When executed by at least one processor of a system for MR T1 mapping, the at least one set of instructions may direct the at least one processor to perform a method. The method may include: obtaining at least three images of a subject acquired within an inversion recovery (IR) process, each image of the at least three images being acquired within a cardiac cycle during a breath-hold of the subject; and determining a T1 map of the subject based on the at least three images acquired within the IR process and a trained model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 8 is a flowchart illustrating an exemplary process for determining a T1 map according to some embodiments of the present disclosure;

FIG. 9 is a flowchart illustrating an exemplary process for generating a trained model according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
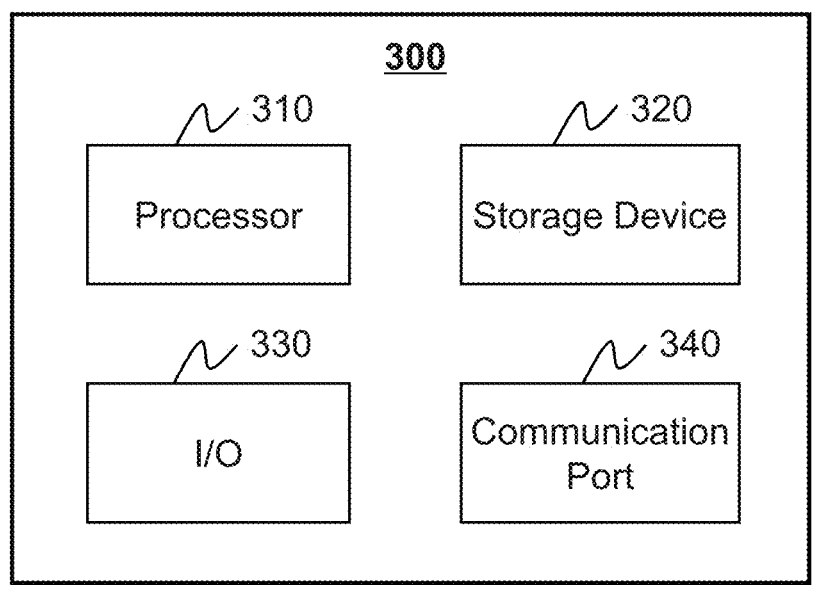
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "imaging modality" or "modality" as used herein broadly refers to an imaging method or technology that gathers, generates, processes, and/or analyzes imaging information of a subject. The subject may include a biological subject and/or a non-biological subject. The biological subject may be a human being, an animal, a plant, or a portion thereof (e.g., a heart, a breast, etc.). In some embodiments, the subject may be a man-made composition of organic and/or inorganic matters that are with or without life.

Provided herein are systems and methods for non-invasive biomedical imaging, such as for disease diagnostic or research purposes. While the systems and methods disclosed in the present disclosure are described primarily regarding a system for MR T1 mapping. It should be understood that this is only for illustration purposes. The systems and methods of the present disclosure may be applied to any other kind of imaging system. In some embodiments, the imaging system may include a single modality imaging system and/or a multi-modality imaging system. The single modality imaging system may include, for example, the MRI system. The multi-modality imaging system may include, for example, an X-ray imaging-magnetic resonance imaging (X-ray-MRI) system, a single photon emission computed tomography-magnetic resonance imaging (SPECT-MRI) system, a digital subtraction angiography-magnetic resonance imaging (DSA-MRI) system, a computed tomography-magnetic resonance imaging (MRI-CT) system, a positron emission tomography-magnetic resonance imaging (PET-MRI) system, etc.

An aspect of the present disclosure relates to systems and methods for MR T1 mapping. The systems and methods may obtain at least three images of a subject acquired within an inversion recovery (IR) process, and determine a T1 map of the subject based on the at least three images acquired within the IR process and a trained model. Each image of the at least three images may be acquired within a cardiac cycle during one breath-hold of the subject. In this way, the subject may hold his/her breath for only a few cardiac cycles, thereby improving the comfort of the subject during the imaging process and ease of the imaging process. At the same time, a reduced amount of image data with improved reliability obtained in the imaging process may improve the efficiency of the imaging process, the subsequent image processing, and the accuracy of a T1 map determined on the basis of the image data so acquired.

Figure 1:
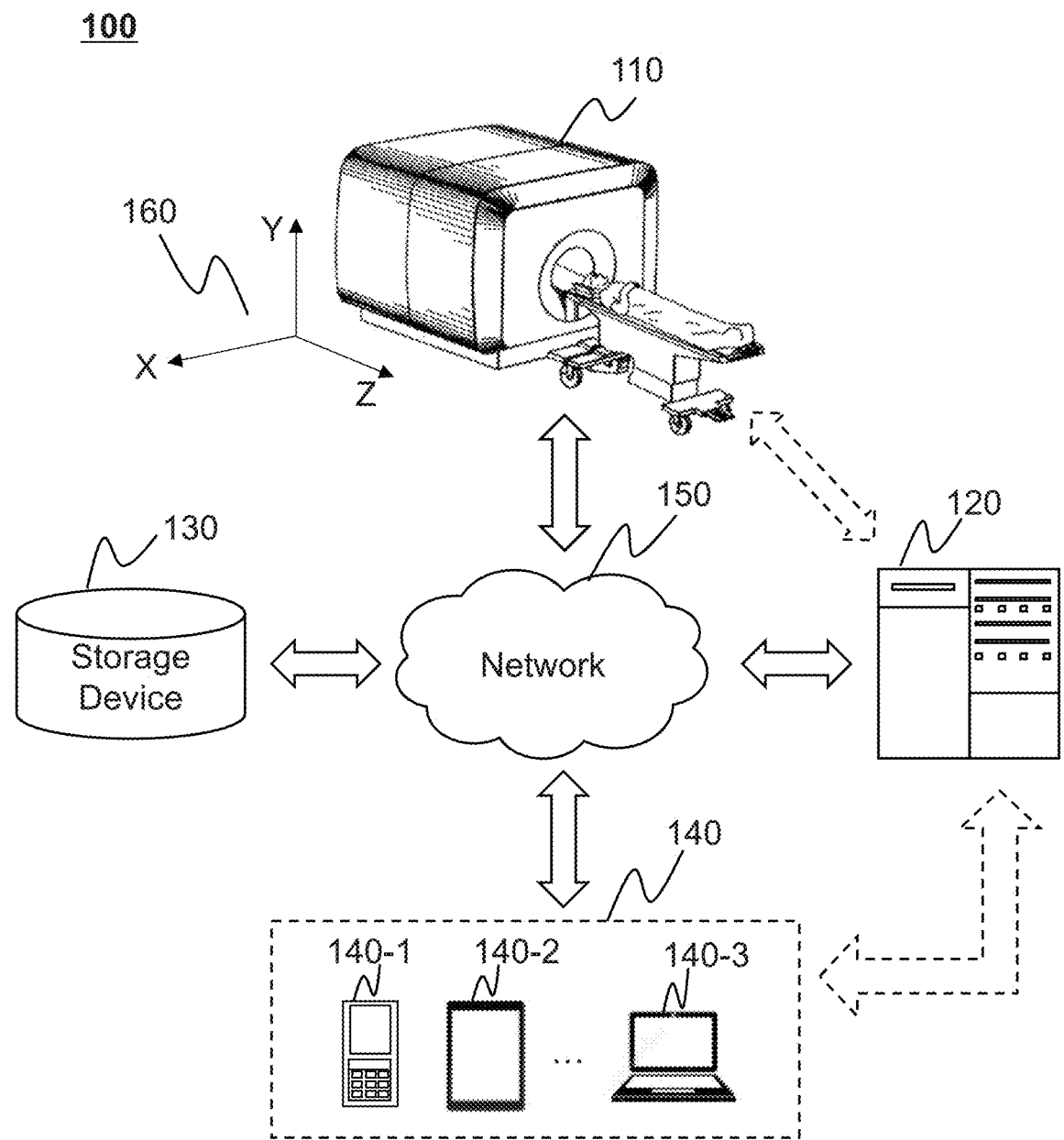
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MRI scanner 110, a processing device 120, a storage device 130, one or more terminals 140, and a network 150. In some embodiments, the MRI scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MRI scanner 110 may be connected to the processing device 120 through the network 150. As another example, the MRI scanner 110 may be connected to the processing device 120 directly.

The MRI scanner 110 may be configured to scan a subject (or a part of the subject) to acquire image data of the subject. In some embodiments, the MRI scanner 110 may include, for example, a main magnet, a gradient coil (or also referred to as a spatial encoding coil), a radio frequency (RF) coil, etc., as described in connection with FIG. 2. In some embodiments, the MRI scanner 110 may be a permanent magnet MRI scanner, a superconducting electromagnet MRI scanner, or a resistive electromagnet MRI scanner, etc., according to types of the main magnet. In some embodiments, the MRI scanner 110 may be a high-field MRI scanner, a mid-field MRI scanner, and a low-field MRI scanner, etc., according to the intensity of the magnetic field. More description of the MRI scanner 110 may be found elsewhere in the present disclosure. See, e.g., FIG. 2 and the description thereof.

The subject scanned by the MRI scanner 110 may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, heart, stomach, blood vessel, soft tissue, knee, feet, or the like, or a combination thereof.

For illustration purposes, a coordinate system 160 including an X axis, a Y-axis, and a Z-axis is provided in FIG. 1. The X axis and the Z axis shown in FIG. 1 may be horizontal, and the Y-axis may be vertical. As illustrated, the positive X direction along the X axis may be from the right side to the left side of the MRI scanner 110 seen from the direction facing the front of the MRI scanner 110; the positive Y direction along the Y axis shown in FIG. 1 may be from the lower part to the upper part of the MRI scanner 110; the positive Z direction along the Z axis shown in FIG.

1 may refer to a direction in which the subject is moved out of the scanning channel (or referred to as the bore) of the MRI scanner 110.

The processing device 120 may process data and/or information obtained from the MRI scanner 110, the storage device 130, and/or the terminal(s) 140. For example, the processing device 120 may obtain at least three images of the subject, or image data corresponding to the at least three images acquired after an inversion recovery pulse is applied to the subject (and before another IR pulse is applied), or referred to as within an inversion recovery (IR) process. Image data corresponding to each image of the at least three images may be acquired within a cardiac cycle during one breath-hold of the subject. As another example, the processing device 120 may determining a T1 map of the subject based on the at least three images acquired within one IR process and a trained model. In some embodiments, the processing device 120 may be a single server or a server group. The server group may be centralized or distributed. In some embodiments, the processing device 120 may be local or remote. For example, the processing device 120 may access information and/or data from the MRI scanner 110, the storage device 130, and/or the terminal(s) 140 via the network 150. As another example, the processing device 120 may be directly connected to the MRI scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MRI scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MRI scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable user interaction between a user and the MRI system 100. For example, the terminal(s) 140 may receive, from the user, an instruction to cause the MRI scanner 110 to scan the subject. As another example, the terminal(s) 140 may receive a processing result (e.g., a T1 map of the subject) from the processing device 120 and display the processing result to the user. In some embodiments, the terminal(s) 140 may be connected to and/or communicate with the MRI scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MRI scanner 110.

The network 150 may include any suitable network that can facilitate the exchange of information and/or data for the MRI system 100. In some embodiments, one or more components of the MRI system 100 (e.g., the MRI scanner 110, the processing device 120, the storage device 130, the terminal(s) 140, etc.) may communicate information and/or data with one or more other components of the MRI system 100 via the network 150. For example, the processing device 120 may obtain image data (e.g., at least three images of the subject) from the MRI scanner 110 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MRI scanner 110. As another example, a component of the MRI system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

Figure 2:
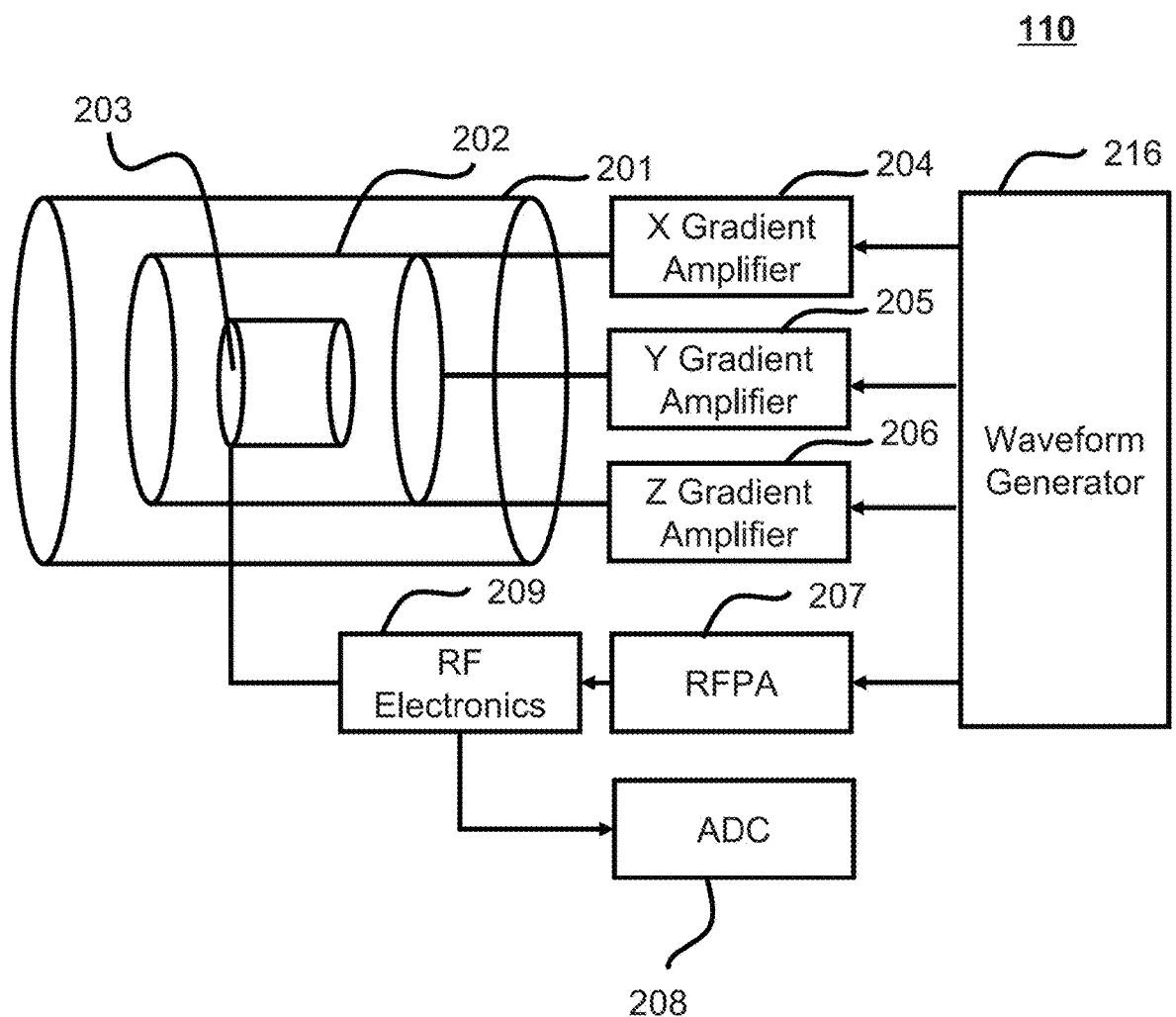
FIG. 2 is a schematic diagram illustrating an exemplary MRI scanner according to some embodiments of the present disclosure.

FIG. 2 is a schematic diagram illustrating an exemplary MRI scanner 110 according to some embodiments of the present disclosure. One or more components of the MRI scanner 110 are illustrated in FIG. 2. As illustrated, main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the subject is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of the subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI scanner 110 may further include a subject positioning system (not shown). The subject positioning system may include a subject cradle and a transport device. The subject may be placed on the subject cradle and be positioned by the transport device within the bore of the main magnet 201.

MRI systems (e.g., the MRI system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MRI image. As used herein, T1 relaxation refers to the process in which the net magnetization grows/returns to its initial maximum value parallel to the main magnetic field. T1 value may be the time constant for regrowth of longitudinal magnetization (e.g., along the main magnetic field). As used herein, T2 relaxation refers to the process in which the transverse components of magnetization decay or dephase. T2 value may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice."

Typically, portions of the patient's body to be imaged are scanned by a sequence of measurement cycles in which the RF excitation signals and the magnetic field gradients Gx, Gy, and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include a spin echo sequence, a gradient echo sequence, a diffusion sequence, an inversion recovery (IR) pulse sequence, or the like, or any combination thereof. For instance, the spin echo sequence may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequence may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. As used herein, the IR pulse sequence may be a conventional spin echo sequence preceded by a 180° inverting pulse. The protocol may also include information regarding image contrast and/or ratio, an ROI, slice thickness, an imaging type (e.g., T1 weighted imaging, T2 weighted imaging, proton density weighted imaging, etc.), T1 value, T2 value, an echo type (e.g., spin echo, fast spin echo (FSE), fast recovery FSE, single shot FSE, gradient recalled echo, fast imaging with stead-state procession, etc.), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

FIG. 3 is a schematic diagram illustrating exemplary hardware and/or software components of a computing device 300 according to some embodiments of the present disclosure. The computing device 300 may be used to implement any component of the MRI system 100 as described herein. For example, the processing device 120 and/or the terminal 140 may be implemented on the computing device 300, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 3, the computing device 300 may include a processor 310, a storage device 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data obtained from the MRI scanner 110, the terminal(s) 140, the storage device 130, and/or any other component of the MRI system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage device 320 may store data/information obtained from the MRI scanner 110, the terminal(s) 140, the storage device 130, and/or any other component of the MRI system 100. In some embodiments, the storage device 320 may include a mass storage device, a removable storage device, a volatile read-and-write memory, a read-only memory (ROM), or the like, or any combination thereof. In some embodiments, the storage device 320 may store one or more programs and/or instructions to perform exemplary methods described in the present disclosure. For example, the storage device 320 may store a program for the processing device 120 to execute for SMS multitasking imaging.

The I/O 330 may input and/or output signals, data, information, etc. In some embodiments, the I/O 330 may enable a user interaction with the processing device 120. In some embodiments, the I/O 330 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 150) to facilitate data communications. The communication port 340 may establish connections between the processing device 120 and the MRI scanner 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
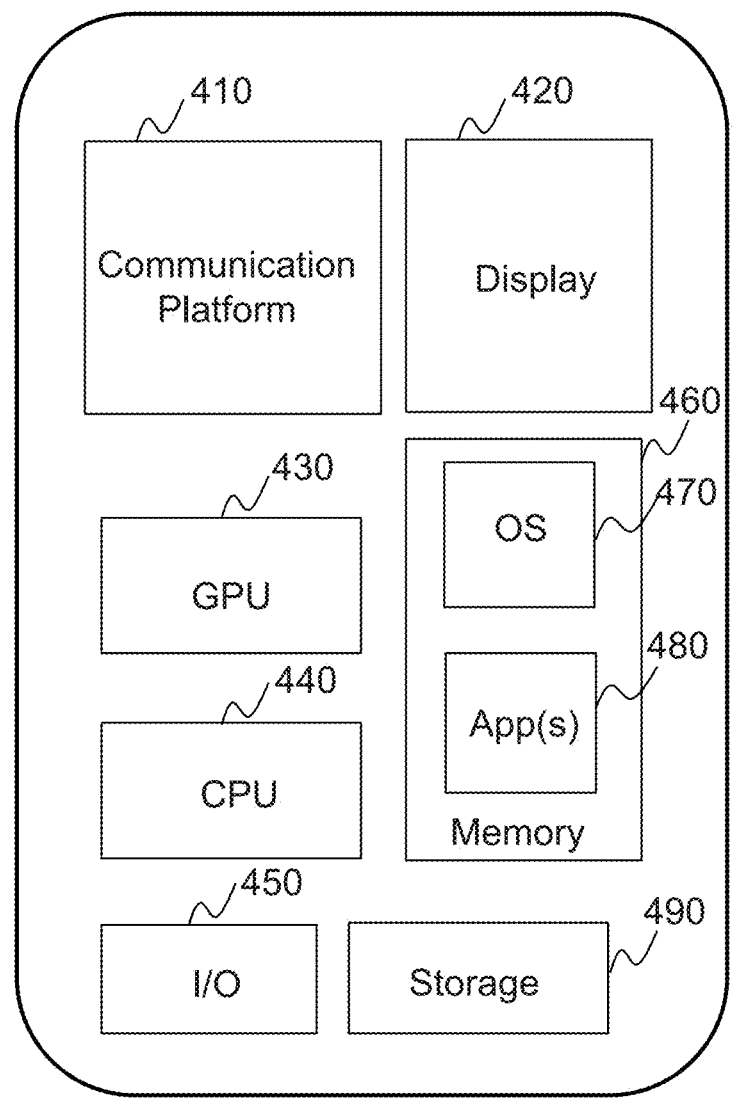
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 140 and/or the processing device 120) of the MRI system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5A:
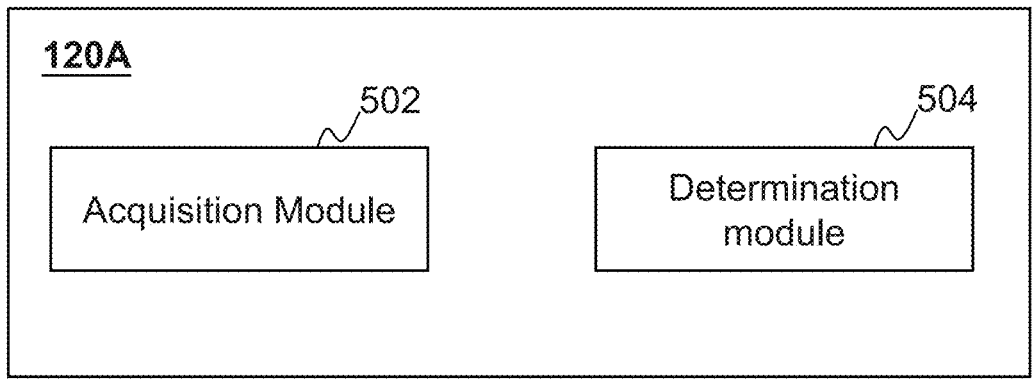
FIG. 5A is a block diagram illustrating an exemplary processing device according to some embodiments of the present disclosure.
Figure 5B:
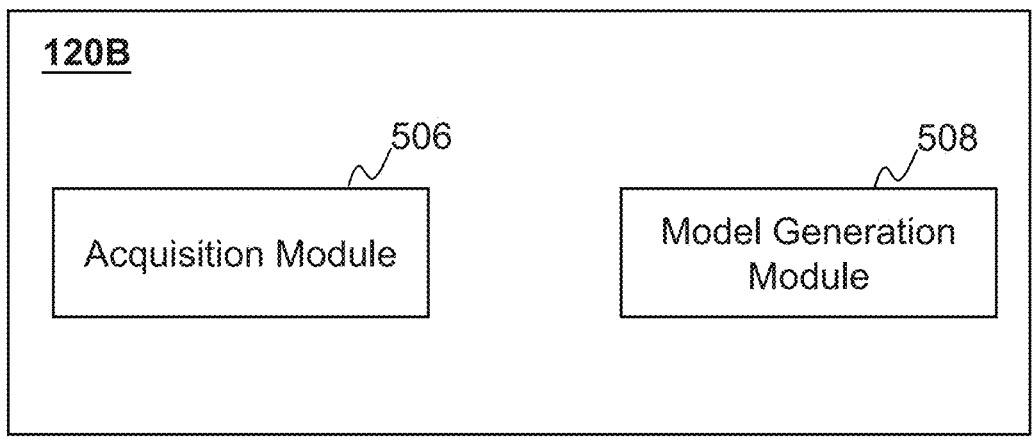
FIG. 5B is a block diagram illustrating an exemplary processing device according to some embodiments of the present disclosure.

FIGS. 5A and 5B are block diagrams illustrating exemplary processing device 120A and 120B according to some embodiments of the present disclosure.

The processing device 120A and 120B may be exemplary processing devices 120 as described in connection with FIG. 1. In some embodiments, the processing device 120A may be configured to apply one or more machine learning models in generating an artifact corrected image of an original image. The processing device 120B may be configured to generate the one or more machine learning models. In some embodiments, the processing device 120A and 120B may be respectively implemented on a processing unit (e.g., a processor 310 illustrated in FIG. 3 or a CPU 440 as illustrated in FIG. 4). Merely by way of example, the processing device 120A may be implemented on a CPU 440 of a terminal device, and the processing device 120B may be implemented on a computing device 300. Alternatively, the processing device 120A and 120B may be implemented on a same computing device 300 or a same CPU 440. For example, the processing device 120A and 120B may be implemented on a same computing device 300.

As shown in FIG. 5A, the processing device 120A may include an acquisition module 502 and a determination module 504.

The acquisition module 502 may be configured to obtain at least three images of a subject, or image data corresponding to the at least three images. The image data may be acquired within one IR process. That is, the image data may be acquired after an inversion recovery (IR) pulse is applied to the subject and before a next IR pulse is applied.

The determination module 504 may be configured to determine a T1 map of the subject based on the at least three images acquired within the IR process and a trained model. For example, the determination module 504 may determine a T1 value by inputting, into the trained model, at least three values of elements each of which is at a corresponding element location in one of the at least three images and an image acquisition time of each of the at least three images. As another example, the determination module 504 may determine the T1 map based on a plurality of T1 values of a plurality of element locations in the T1 map. More descriptions regarding determining the T1 map may be found elsewhere in the present disclosure. See, e.g., FIG. 6 and the descriptions thereof.

As shown in FIG. 5B, the processing device 120B may include an acquisition module 506 and a model generation module 508.

The acquisition module 506 may be configured to obtain data for training a model. For example, the acquisition module 506 may obtain a plurality of sample sets. each sample set may include a plurality of sample images, a plurality of sample image acquisition times each of which corresponds to one of the series of sample images, and a reference T1 map of the plurality of sample images.

The model generation module 508 may be configured to generate a model. For example, the model generation module 508 may generate a trained model by training a preliminary model based on the plurality of sample sets obtained from the acquisition module 506. More descriptions regarding the model training may be found elsewhere in the present disclosure. See, e.g., FIG. 9 and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120A and/or the processing device 120B may share two or more of the modules, and any one of the modules may be divided into two or more units. For instance, the processing device 120A and 120B may share a same acquisition module; that is, the acquisition module 502 and the acquisition module 506 are a same module. In some embodiments, the processing device 120A and/or the processing device 120B may include one or more additional modules, such as a storage module (not shown) for storing data. In some embodiments, the processing device 120A and the processing device 120B may be integrated into one processing device 120.

Figures 6, 7:
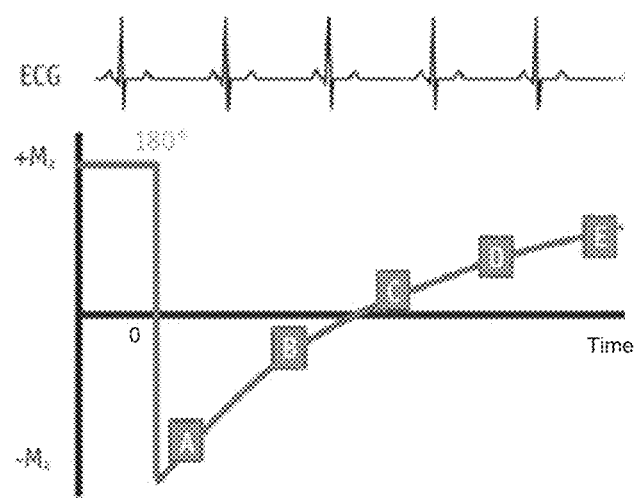
FIG. 6 is a flowchart illustrating an exemplary process for determining a T1 map according to some embodiments of the present disclosure.
FIG. 7 is a schematic diagram illustrating an exemplary scanning process within one IR process according to some embodiments of the present disclosure.

FIG. 6 is a flowchart illustrating an exemplary process 600 for determining a T1 map according to some embodiments of the present disclosure. In some embodiments, the process 600 may be executed by the MRI system 100. For example, the process 600 may be implemented as a set of instructions (e.g., an application) stored in a storage device (e.g., the storage device 130, the storage device 320, and/or the storage 490). In some embodiments, the processing device 120A (e.g., the processor 310 of the computing device 300, the CPU 440 of the mobile device 400, and/or one or more modules illustrated in FIG. 5A) may execute the set of instructions and may accordingly be directed to perform the process 600. The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 602, the processing device 120A (e.g., the acquisition module 502) may obtain at least three images of a subject, or image data corresponding to the at least three images. The image data may be acquired within one IR process. That is, the image data may be acquired after an inversion recovery (IR) pulse is applied to the subject and before a next IR pulse is applied.

In some embodiments, a subject may include a biological subject and/or a non-biological subject. For example, the subject may include a body or a specific portion (e.g., a thorax, a heart, etc.) of the body. In some embodiments, the image data corresponding to the at least three images may be obtained from an MRI scanner (e.g., the MRI scanner 110). For example, the MRI scanner 110 may scan the subject to generate the image data corresponding to the at least three images. As used herein, the image data of or corresponding to an image refers to the image data on the basis of which the image is generated by way of, e.g., image reconstruction, or other image processing algorithms or methods. During a scanning process, the subject may be asked to hold his/her breath for a plurality of cardiac cycles. In some embodiments, the image data may be acquired within one IR process. After the subject begins to hold his/her breath (and keeps still), an IR pulse may be applied to the subject to perform the IR process. In an IR process, the magnetizations within the subject may be inverted after a 180° inverting pulse is applied to the subject. As used herein, the IR pulse may be a conventional spin echo sequence preceded by a 180° inverting pulse. For example, the IR pulse generated by the waveform generator 216 of the MRI scanner 110 may be applied to the RF coils 230, and the RF coils 230 may generate RF signals that provide a third magnetic field that is utilized to generate echo signals related to the subject being scanned. In some embodiments, an electrocardiogram (ECG) recording may be simultaneously conducted during the scanning process. The image data of each image of the at least three images may be acquired within a cardiac cycle during the single breath-hold of the subject. FIG. 7 is a schematic diagram illustrating an exemplary scanning process within one IR process according to some embodiments of the present disclosure. As shown in FIG. 7, an ECG recording is simultaneously conducted during the scanning process. Image data of five images may be acquired at time point A, time point B, time point C, time point D, and time point E, respectively, when the subject holds his/her breath and the IR pulse is applied. Each of the five time points A-E may be within a cardiac cycle of the subject, respectively, according to the ECG recording. It should be noted that FIG. 7 is only for illustration purposes, other image count of the at least three images may be acquired within one IR process. For example, the image count of the at least three images may be three, four, five, six, seven, eight, nine, ten, etc.

In some embodiments, the image data of each image of the at least three images may be acquired when the subject is in a certain state within each cardiac cycle. The certain state may be detected according to the ECG recording. For example, when an R wave is detected in the ECG recording during a cardiac cycle, the image data corresponding to an image of the at least three images may be acquired. In some embodiments, the image data corresponding to each image of the at least three images may be acquired at a certain time point within each cardiac cycle. For example, within each cardiac cycle of 100 ms, the image data corresponding to each of the at least three images may be acquired at the $60^{th}$ ms since the onset of the cardiac cycle within the 100-ms cardiac cycle. In some embodiments, the processing device 120A may determine whether the heartbeats of the subject are regular and periodic (or the cardiac cycles are the same). In response to a determination that the heartbeats of the subject are regular and periodic, the processing device 120A may cause the image data of each of the at least three images to be acquired at a certain time point within each cardiac cycle. Otherwise, the processing device 120A may cause the image data of each of the at least three images to be acquired when the subject is in a certain state within each cardiac cycle.

In some embodiments, each of the at least three images may be labeled with an image acquisition time. The image acquisition time may be a time point at which the image data of the image is acquired during the IR process. For example, as shown in FIG. 7, image data of a first image of the at least three images is acquired at the time point A after the IR pulse is applied at time point 0. The first image of the at least three images may be labeled with time point A. The image acquisition time may provide information regarding relative time points with respect to a reference time point (e.g., the onset of an IR pulse) within an IR process.

In some embodiments, the at least three images may be original images (e.g., 2D images or 3D images) based on image data acquired from the MRI scanner 110 directly. For example, the at least three images may be reconstructed based on the image data acquired from the MRI scanner 110. In some embodiments, the at least three images may be processed images of the original images. For example, the processing device 120A may process one or more of the at least three original images to obtain one or more processed images. In some embodiments, the one or more processed images may be obtained by correcting artifacts in the one or more of the at least three original images. For example, the processing device 120A may correct artifacts caused by movements (e.g., heartbeats) of the subject during the scanning process in the one or more of the at least three original images by performing a motion correction algorithm. Exemplary motion correction algorithms may include an iterative convergence algorithm, a contour tracking algorithm, a minimum entropy-based algorithm, or the like, or any combination thereof. As another example, the processing device 120A may correct artifacts caused by hardware (e.g., an inhomogeneous magnetic field, an eddy current) of the MRI scanner 110 in the one or more of the at least three original images by performing a phase correction algorithm. Exemplary phase correction algorithms may include a spectral peak location algorithm, a peak curve fitting algorithm, a minimum entropy-based algorithm, a minimization of peak regularity algorithm, or the like, or any combination thereof. In some embodiments, for each image of the at least three original images, the processing device 120A may obtain a real part image and an imaginary part image of the image. For example, the image may correspond to image data that have a real part and an imaginary part. An inverse Fourier transform may be performed on the real part of the image data and the imaginary part of the image data of the image, respectively, to obtain the real part image and the imaginary part image of the image. The processing device 120A may register the real part image with other real part images of other images of the at least three original images, and register the imaginary part image with other imaginary part images of the at least three original images (e.g., by performing the phase correction algorithm), respectively. A registered real part image and a registered imaginary part image of a same original image may be fused/combined to obtain a processed image.

In some embodiments, the processing device 120A may process each image of the at least three original images to obtain at least three processed images. In some embodiments, the processing device 120A may select one or more images from the at least three original images to process. For example, the processing device 120A may identify an artifact type in an original image and process the original image by correcting artifacts of the identified artifact type. For example, if the artifacts in the original image are periodic, the processing device 120A may determine that the artifacts may be caused by the heartbeats of the subject, and the processing device 120A may process the original image according to a motion correction algorithm. As another example, if the artifacts in the original image are Moiré patterns, the processing device 120A may determine that the artifacts may be caused by an inhomogeneous magnetic field of the MRI scanner 110, and the processing device 120A may process the original image according to a phase correction algorithm. In some embodiments, the processing device 120A may perform at least one of a motion correction algorithm or a phase correction algorithm on the one or more images of the at least three images. For example, the processing device 120A may process one or more images of the at least three original images by performing both the phase correction algorithm and the motion correction algorithm. As another example, the processing device 120A may process each image of the at least three original images by performing the phase correction algorithm and select one or more processed images thereof to further perform the motion correction algorithm. It should be noted that the phase correction algorithm and/or the motion correction algorithm are only for illustration purposes, other algorithm may also be performed to process one or more of the at least three images.

In some embodiments, an image count of the at least three images may be associated with a cycle count of the plurality of cardiac cycles during the breath-hold of the subject. In some embodiments, image data of one of the at least three images may be acquired during one cardiac cycle. For example, the image count of the at least three images may be lower than or equal to the cycle count of the plurality of cardiac cycles during the breath-hold of the subject. For example, the subject holds his/her breath for four cardiac cycles during the scanning process, and the image count of the at least three images may be four. Each of the four images may be obtained within each cardiac cycle of the four cardiac cycles. As another example, the subject holds his/her breath for four cardiac cycles during the scanning process, and the image count of the at least three images may be three. The processing device 120A may select, from the four cardiac cycles, three cardiac cycles in each of which a certain state of the subject is detected. Each of the three images may be obtained within each cardiac cycle of the selected three cardiac cycles.

In some embodiments, the at least three images may be previously generated based on image data acquired by the MRI scanner 110 and stored in a storage device (e.g., the storage device 130, the storage device 320, the storage 490, or an external source). The processing device 120A may retrieve the at least three images directly from the storage device.

In 604, the processing device 120A (e.g., the determination module 504) may determine a T1 map of the subject based on the at least three images acquired within the IR process and a trained model.

In some embodiments, the T1 map may be a parametric map showing T1 values of the subject at element locations (e.g., pixel locations, voxel locations) of the parametric map. In some embodiments, a T1 value may correspond to an element (e.g., a pixel, a voxel) at an element location (e.g., a pixel location, a voxel location) in each of the at least three images. For example, for at least three elements each of which is at a same element location in one of the at least three images, the T1 map may include a T1 value of a component at the same element location on the T1 map as the image. As used herein, a same element location in different images or in an image and a corresponding T1 map of a subject represents a same physical point or location of the subject. In some embodiments, the T1 map may include T1 values arranged in a component array of a same array dimension of elements of each image of the at least three images. For example, each image of the at least three images includes elements (e.g., pixels) arranged in an array dimension of m×n, in which each of m and n is an integer equal to or greater than 1, respectively. Accordingly, the T1 map may include T1 values arranged in the array dimension of m×n. A T1 value at element location (p, q) of the T1 map may correspond to (e.g., determined based on) values of elements (e.g., pixels) at the element location (p, q) in each of the at least three images, in which p is an integer and 1≤p≤m, and q is an integer and 1≤q≤n.

In some embodiments, the trained model may be a process or an algorithm for processing the at least three images to obtain the T1 map of the subject. In some embodiments, the trained model may include a Fully Connected Neural Network (FNN), a Deep Neural Network (DNN), a Convolutional Neural Network (CNN), a Recurrent Neural Network (RNN), a Feature Pyramid Network (FPN), a Generative Adversarial Network (GAN), a CycleGAN model, a pix2pix model, or the like, or any combination thereof. In some embodiments, the trained model may be generated according to a machine learning algorithm as described elsewhere in the present disclosure (e.g., FIG. 9 and the descriptions thereof).

In some embodiments, the processing device 120A may obtain the trained model from one or more components of the MRI system 100 (e.g., the storage device 130, the storage device 320, the storage 490, or an external source via a network (e.g., the network 150)). For example, the trained model may be previously trained by a computing device (e.g., the processing device 120B), and stored in a storage device (e.g., the storage device 130, the storage device 320, the storage 490, or an external source) of the MRI system 100. The processing device 120A may access the storage device and retrieve the trained model.

In some embodiments, the trained model may include a process or an algorithm for both processing the at least three images and determining the T1 map of the subject. For example, the trained model may be generated by training a preliminary model using a plurality of sample sets. Each of the plurality of sample sets may include a plurality of sample images (also referred to as sample original images) and a reference T1 map of the plurality of sample images. In some embodiments, the processing device 120A may obtain the T1 map of the subject by inputting the at least three images into the trained model. For example, the processing device 120A may input the at least three images into the trained model, and the trained model may output the T1 map directly. In some embodiments, each of the plurality of sample sets may further include a sample image acquisition time at which each sample image of the plurality of sample images is acquired during a sample IR process. During a sample IR process, a sample IR pulse is applied to a sample subject. The processing device 120A may input the at least three images and an image acquisition time of each image of the at least three images into the trained model, and the trained model may output the T1 map.

In some embodiments, the processing device 120A may determine a T1 values at each element location of the T1 map based on the trained model directly, and determine the T1 map based on a plurality of T1 values at a plurality of element locations. In some embodiments, the T1 map may be determined according to an exemplary process as described elsewhere in the present disclosure (e.g., FIG. 8 and the descriptions thereof).

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, the process 600 may include an additional operation to transmit the T1 map to a terminal device (e.g., a terminal device 140 of a doctor) for display.

FIG. 8 is a flowchart illustrating an exemplary process 800 for determining a T1 map according to some embodiments of the present disclosure. In some embodiments, the process 800 may be executed by the MRI system 100. For example, the process 800 may be implemented as a set of instructions (e.g., an application) stored in a storage device (e.g., the storage device 130, the storage device 320, and/or the storage 490). In some embodiments, the processing device 120A (e.g., the processor 310 of the computing device 300, the CPU 440 of the mobile device 400, and/or one or more modules illustrated in FIG. 5A) may execute the set of instructions and may accordingly be directed to perform the process 800. The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, for an element location in a T1 map, the processing device 120A (e.g., the determination module 504) may determine a T1 value by inputting, into the trained model, at least three values of elements each of which is at a corresponding element location in one of the at least three images and an image acquisition time of each of the at least three images.

In some embodiments, the trained model may include a process or an algorithm for determining T1 values of a plurality of element locations of a T1 map. For example, the trained model may be generated by training a preliminary model using a plurality of sample sets. Each of the plurality of sample sets may include a plurality of sample values (e.g., sample pixel values, sample voxel values, sample gray values, etc.) of sample elements (e.g., sample pixels, sample voxels) at a sample element location of a plurality of sample images and a reference T1 value of the plurality of sample values. The reference T1 value may be a desired output of the trained model when the plurality of sample values are input into the trained model. In some embodiments, each of the plurality of sample sets may further include a sample image acquisition time at which each sample image of the plurality of sample images is acquired during a sample IR process. During a sample IR process, a sample IR pulse is applied to a sample subject. More descriptions regarding the model training may be found elsewhere in the present disclosure. See, e.g., FIG. 9 and the descriptions thereof.

In some embodiments, the T1 map may include a plurality of components (e.g., T1 values) arranged at a plurality of element locations. To determine the T1 map, a component (e.g., a T1 value) at each element location may be determined. In some embodiments, the processing device 120A may obtain a T1 value at an element location corresponding to the element location by inputting, into the trained model, at least three values of elements each of which is at a corresponding element location in one of the at least three images, and the trained model may output the T1 value. For example, for each image of the at least three images, the processing device 120A may identify a value (e.g., a pixel value, a voxel value, a gray value, etc.) of an element (e.g., a pixel, a voxel) at each element location (e.g., a pixel location, a voxel location) of the image. The processing device 120A may input, into the trained model, at least three values (e.g., pixel values) of elements (e.g., pixels) at element location (p, q) of each of the at least three images. The trained model may output a T1 value for the element location (p, q) of the T1 map.

In some embodiments, the inputs of the trained model may further include an image acquisition time of each of the at least three images. For example, the processing device 120A may identify an image acquisition time of each image of the at least three images). In some embodiments, the image acquisition time of an image may be a time point at which the image data of the image is acquired during one IR process. In some embodiments, the processing device 120A may input, into the trained model, the at least three values of elements at least three corresponding element locations each of which is in one of the at least three images and an image acquisition time of each of the at least three images, and the trained model may output the T1 value. For example, if the image count of the at least three images is N, an input count of inputs of the trained model for determining a T1 value may be 2N, in which N is an integer equal to or greater than 3. Among the 2N inputs, N inputs include N image acquisition times of the N images, and the other N inputs include N values of elements each of which is at a same element location of one of the N images.

In 804, the processing device 120A (e.g., the determination module 504) may determine the T1 map based on a plurality of T1 values of a plurality of element locations in the T1 map.

In some embodiments, the processing device 120A may generate the T1 map by arranging each of the plurality of T1 values at an element location of the plurality of element locations. For example, for at least three elements each of which is at a same element location in one of the at least three images, the T1 map may include a T1 value arranged at the same element location on the T1 map. For example, each image of the at least three images includes elements (e.g., pixels) arranged in an array dimension of m×n, in which each of m and n is an integer equal to or greater than 1, respectively. Accordingly, the T1 map may include T1 values arranged in the array dimension of m×n. A T1 value at element location (p, q) of the T1 map may correspond to (e.g., determined based on) values of elements (e.g., pixels) at element location (p, q) in each of the at least three images, in which p is an integer and 1≤p≤m, and q is an integer and 1≤q≤n.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 800 may be accomplished with one or more additional operations not described and/or without one or more of the operations discussed above. For example, the process 800 may include an additional operation to transmit the T1 map to a terminal device (e.g., a terminal device 140 of a doctor) for display.

FIG. 9 is a flowchart illustrating an exemplary process 900 for generating a trained model according to some embodiments of the present disclosure. In some embodiments, the process 900 may be executed by the MRI system 100. For example, the process 900 may be implemented as a set of instructions (e.g., an application) stored in a storage device (e.g., the storage device 130, the storage device 320, and/or the storage 490). In some embodiments, the processing device 120B (e.g., the processor 310 of the computing device 300, the CPU 440 of the mobile device 400, and/or one or more modules illustrated in FIG. 5B) may execute the set of instructions and may accordingly be directed to perform the process 900. In some embodiments, the trained model described in connection with operation 604 in FIG. 6 may be obtained according to the process 900. In some embodiments, the process 900 may be performed by another device or system other than the MRI system 100, e.g., a device or system of a vendor or a manufacturer of the trained model. For illustration purposes, the implementation of the process 900 by the processing device 120B is described as an example.

In some embodiments, the trained model may be trained offline. For example, the trained model may be trained and stored in a storage device (e.g., the storage device 130, the storage device 320, and/or the storage 490) of the MRI system 100. The processing device 120B may access the storage device to retrieve the trained model for determining the T1 map. Alternatively, the trained model may be trained in real-time. For example, the processing device 1206 may train the trained model when the trained model is needed for generating a T1 map.

In 902, the processing device 1206 (e.g., the acquisition module 506) may obtain a plurality of sample sets.

In some embodiments, each sample set may include a plurality of sample images, a plurality of sample image acquisition times each of which corresponds to one of the series of sample images, and a reference T1 map of the plurality of sample images. In a sample set, the reference T1 map may be determined based on the plurality of sample images and the plurality of sample image acquisition times. In some embodiments, each sample set may include a plurality of values of sample elements each of which is at a sample element location of one of the plurality of sample images, a plurality of sample image acquisition times each of which corresponds to one of the sample images, and a reference T1 value corresponding to the sample element location. In a sample set, the reference T1 value may be determined based on the plurality of values of sample elements and the plurality of sample image acquisition times.

In some embodiments, for a sample set of the plurality of sample sets, the processing device 1206 may determine the reference T1 map based on the plurality of sample images and the plurality of sample image acquisition times of the sample set. For example, for a sample set, the processing device 1206 may obtain a plurality of sample images of a sample subject. The plurality of sample images may be generated based on sample image data acquired by a sample MRI scanner. In some embodiments, the sample image data of the plurality of sample images of the sample set may be acquired using a Modified Look-Locker Inversion Recovery (MOLLI) sequence. In some embodiments, different sample sets may be obtained from different sample MRI scanners. In some embodiments, the sample MRI scanner may be a same device (or a same product model) with the MRI scanner that obtain the image data corresponding to the at least three images described in FIG. 6.

Figure 10:
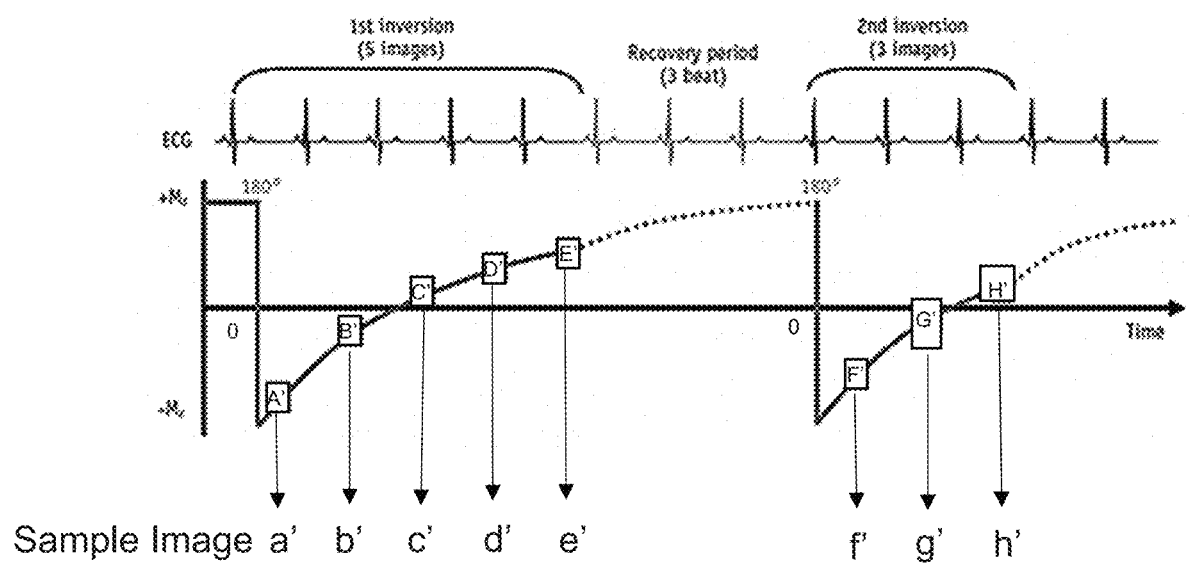
FIG. 10 is a schematic diagram illustrating an exemplary scanning process of applying a MOLLI sequence according to some embodiments of the present disclosure.

FIG. 10 is a schematic diagram illustrating an exemplary scanning process of applying a MOLLI sequence according to some embodiments of the present disclosure. As shown in FIG. 10, an ECG recording is simultaneously conducted during the scanning process. During the scanning process, the sample subject may be asked to hold his/her breath for a plurality of cardiac cycles (e.g., for eleven cardiac cycles as shown in FIG. 10). After the sample subject begins to hold his/her breath (and keeps still), a first sample IR pulse may be applied to the sample subject to perform a first sample IR process. During the first sample IR process, sample image data of five sample images may be acquired at time point A', time point B', time point C', time point D', and time point E', respectively when the sample subject holds his/her breath and the first sample IR pulse is applied. Each of the 5 time points A'-E' may be within a cardiac cycle of the sample subject according to the ECG recording. After acquiring the five images during the first sample IR process, a recovery process of three cardiac cycles may be performed. During the recovery process, the magnetizations within the sample subject may recover to magnetizations before the first sample IR pulse is applied to the sample subject. Then, a second sample IR pulse may be applied to the sample subject to perform a second sample IR process. During the second sample IR process, sample image data of three sample images may be acquired at time point F', time point G', and time point H', respectively, after the recovery process. Each of the three time points F'-H' may be within a cardiac cycle of the sample subject according to the ECG recording. In each sample IR process, the magnetizations within the sample subject may be inverted after a 180° inverting pulse is applied to the sample subject. As used herein, the sample IR pulse may be a conventional spin echo sequence preceded by a 180° inverting pulse. As shown in FIG. 10, sample image data of eight sample images may be acquired within two sample IR processes. It should be noted that FIG. 10 is only for illustration purposes and not intended to limit the scope of the present disclosure. For example, sample image data of other image count (e.g., nine, ten, eleven, twelve, etc.) of the sample images may be acquired within a scanning process of applying a MOLLI sequence. As another example, more than two IR pulses may be applied to the sample subject within a scanning process, and sample image data of an image count of the acquired sample images after each IR pulse may be one, two, three, four, five, etc.

In some embodiments, sample image data of each image of the plurality of sample images may be acquired when the sample subject is in a certain state (e.g., an R wave exists in the ECG recording) within each cardiac cycle or acquired at a certain time point within each cardiac cycle. For example, during the first sample IR process, sample image data of each of the five sample images may be acquired at time point TI1 (e.g., 60 ms) within each cardiac cycle (e.g., 100 ms). During the second sample IR process, sample image data of each of the three sample images may be acquired at time point TI2 (e.g., 70 ms) within each cardiac cycle. In some embodiments, the time point TI1 may be different from the time point TI2. For example, a value of the time point TI2 may exceed a value of the time point TI1. In some embodiments, a time difference between the time point TI1 and the time point TI2 may be determined according to different application scenarios. For example, during a scanning process when the sample subject is injected with a contrast agent, a time difference between the time point TI1 and the time point TI2 may be different from that when the sample subject is not injected any contrast agent. As another example, different sample MR scanners may correspond to different time differences between the time point TI1 and the time point TI2.

In some embodiments, for a sample set of the plurality of sample sets, the processing device 1206 may identify a sample image acquisition time of each of the plurality of sample images. For example, each of the plurality of sample images may be labeled with a sample image acquisition time. The sample image acquisition time may be a time point at which sample image data of the sample image is acquired after the sample subject being applied an IR pulse. For example, as shown in FIG. 10, sample image data of a sample image a' of the plurality of sample images is acquired at the time point A' after the first IR pulse is applied at time point 0. The sample image acquisition time of the sample image a' is the time point A'. Sample image data of a sample image f' of the plurality of sample images is acquired at the time point F' after the second IR pulse is applied at time point 0. The sample image acquisition time of the sample image f' is the time point F'. In some embodiments, the plurality of sample images in a sample set may be arranged in an order according to the sample image acquisition times and the order of the cardiac cycles after an IR pulse is applied to the sample subject in which the sample image acquisition times fall. In some embodiments, the sample image acquisition times may be relative time points with respect to a reference time point (e.g., the onset of an IR pulse) within an IR process. See, e.g., the arrangement of sample images in FIG. 11.

Figure 11:
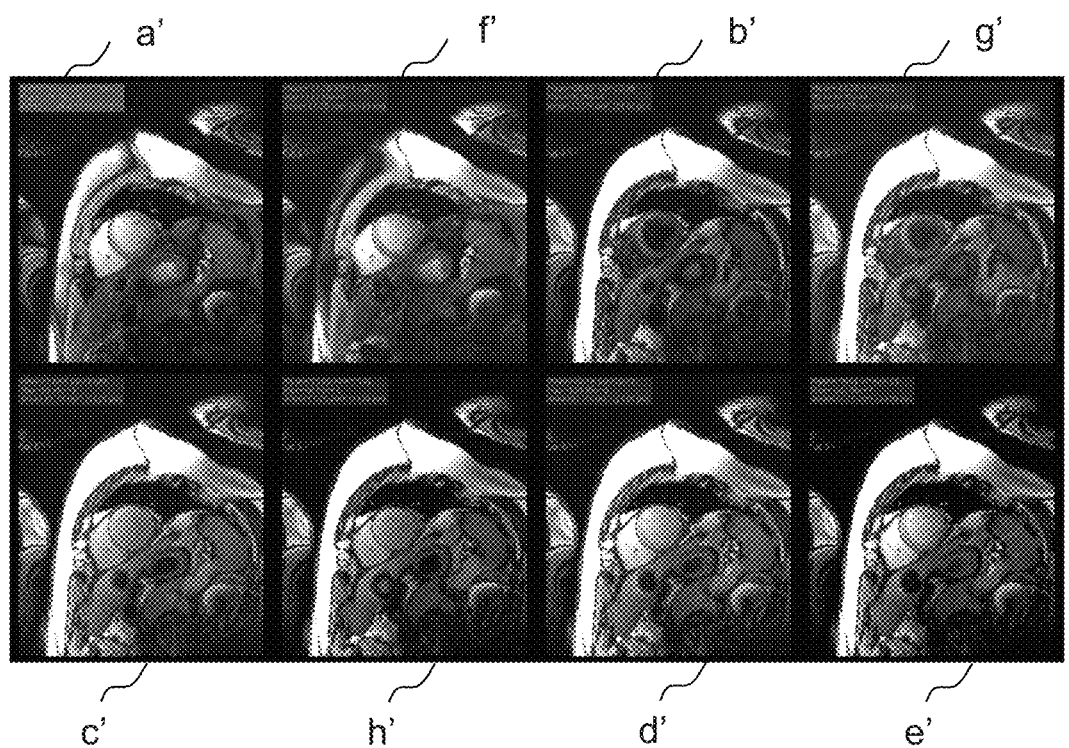
FIG. 11 illustrates exemplary images acquired according to an exemplary scanning process of applying a MOLLI sequence according to some embodiments of the present disclosure.

FIG. 11 illustrates exemplary images acquired according to an exemplary scanning process of applying a MOLLI sequence according to some embodiments of the present disclosure. As described above, during the first sample IR process, each of the five sample images a'-e' may be acquired at time point TI1 within each cardiac cycle, and during the second sample IR process, each of the three sample images f'-h' may be acquired at time point TI2 within each cardiac cycle. A value of the time point TI2 (e.g., 70 ms) may exceed a value of the time point TI1 (e.g., 60 ms). As shown in FIG. 10 and FIG. 11, the eight sample images may be arranged in an order of sample image a', sample image f', sample image b', sample image g', sample image c', sample image h', sample image d', and sample image e'.

In some embodiments, the sample images may be original sample images by image reconstruction performed on the sample image data acquired from sample MRI scanners. In some embodiments, the sample images may be processed sample images of the original sample images. The algorithms for processing a sample image may be described elsewhere in the present disclosure (e.g., FIG. 6 and the relevant descriptions).

In some embodiments, for a sample set of the plurality of sample sets, the processing device 120B may determine the reference T1 map of the plurality of sample images based on the plurality of sample images and the corresponding sample image acquisition times. For example, the processing device 120B may determine the reference T1 map according to a fitting algorithm (e.g., a least square algorithm, an interpolation algorithm, etc.). In some embodiments, the processing device 120B may select a sample element at a same sample element location from each sample image of the plurality of images of the sample set, and determine a reference T1 value at the same sample element location of the reference T1 map. For example, the processing device 120B may select a sample element at sample element location (p', q') from each of the 8 sample images (acquired from the scanning process shown in FIG. 10). A sample value (e.g., a pixel value) of each sample element (e.g., sample pixel) at the sample element location (p', q') may be identified, and a sample image acquisition time of each of the 8 sample images may be identified. The processing device 120B may determine the reference T1 value at sample element location (p', q') according to fitting a curve shown in Equation (1) as below:

$$s(TI) = A - Be^{\frac{-TI}{T^{1*}}}, \quad (1)$$

where TI represents a sample image acquisition time when sample image data of a sample image of a sample set is acquired, s(TI) represents a sample value of a sample element at a sample element location of the sample image whose sample image data is acquired at the sample image acquisition time TI, $T^{1*}$ represents the reference T1 value to be determined, and A and B represent two unknown constants. By inputting the sample image acquisition times of sample images of a sample set and corresponding sample values at a sample element location in each of the sample images into the Equation (1), a reference T1 value corresponding to the sample element location and constants A and B may be determined.

In some embodiments, the processing device 120B may determine a plurality of reference T1 values for a sample set, and generate the sample T1 map by arranging each of the plurality of reference T1 values at a sample element location of reference T1 map. In some embodiments, the generating of the reference T1 map based on a plurality of reference T1 values may be a same or similar to the process for generating a T1 map based on a plurality of T1 values described elsewhere (e.g., FIG. 8 and operation 804) of the present disclosure.

In 904, the processing device 120B (e.g., the model generation module 508) may obtain the trained model by training a preliminary model based on the plurality of sample sets.

In some embodiments, the preliminary model refers to a process, an algorithm, or a model to be trained. The preliminary model may be of any type of model (e.g., a machine learning model) as described elsewhere in the present disclosure (e.g., FIG. 6 and the relevant descriptions). In some embodiments, the processing device 120B may obtain the preliminary model from one or more components of the MRI system 100 (e.g., the storage device 130, the storage device 320, the storage 490, or an external source via a network (e.g., the network 150)).

The preliminary model may include a plurality of model parameters. For example, the preliminary model may be a FNN model and exemplary model parameters of the preliminary model may include the number (or count) of layers, the number (or count) of kernels, a kernel size, a stride, a padding of each convolutional layer, or the like, or any combination thereof. Before training, the model parameters of the preliminary model may have their respective initial values. For example, the processing device 120B may initialize parameter values of the model parameters of the preliminary model.

In some embodiments, the training of the preliminary model may include one or more iterations to iteratively update the model parameters of the preliminary model based on the plurality of sample sets until a termination condition is satisfied in a certain iteration. Exemplary termination conditions may be that the value of a loss function obtained in the certain iteration is less than a threshold value, that a certain count of iterations has been performed, that the loss function converges such that the difference of the values of the loss function obtained in a previous iteration and the current iteration is within a threshold value, etc.

Merely by way of example, an updated preliminary model generated in a previous iteration may be evaluated in the current iteration. The loss function may be used to measure a discrepancy between a predicted T1 map output by the updated preliminary model in the current iteration and the reference T1 map. For example, each sample set may include sample images and a reference T1 map. The sample images of the sample set may be inputted into the updated preliminary model, and the updated preliminary model may output a predicted T1 map. The loss function may be used to measure a difference between the predicted T1 map and the reference T1 map of each sample set. As another example, each sample set may include values of sample elements at a sample element location of each of the plurality of sample images and a reference T1 value. The values of sample elements may be inputted into the updated preliminary model, and the updated preliminary model may output a predicted T1 value. The loss function may be used to measure a difference between the predicted T1 value and the reference T1 value of each sample set. Exemplary loss functions may include a normalized exponential function, a focal loss function, a log loss function, a cross-entropy loss, a squared error loss function, a Dice loss, a L1 loss function, a L2 loss function, or the like.

If the termination condition is not satisfied in the current iteration, the processing device 1206 may further update the updated preliminary model to be used in a next iteration according to, for example, a backpropagation algorithm. If the termination condition is satisfied in the current iteration, the processing device 1206 may designate the updated preliminary model in the current iteration as the trained model.

It should be noted that the above description regarding the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the process 900 may be accomplished with one or more additional operations not described and/or without one or more of the operations discussed above. For example, the process 900 may include an additional operation to store the trained model in a storage device (e.g., the storage device 130, the storage device 320, and/or the storage 490).

Figure 12:
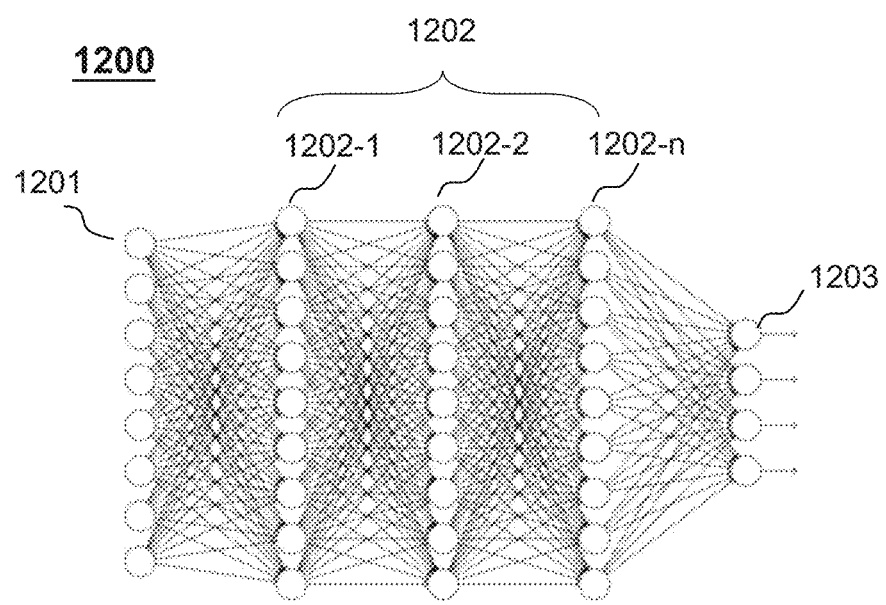
FIG. 12 illustrates a schematic diagram illustrating an exemplary preliminary model according to some embodiments of the present disclosure.

FIG. 12 is a schematic diagram illustrating an exemplary preliminary model 1200 according to some embodiments of the present disclosure. As shown in FIG. 12, the preliminary model 1200 may include an input layer 1201, one or more hidden layers 1202, and an output layer 1203. In some embodiments, the layers of the preliminary model 1200 may be connected in a feed-forward fashion, and an output of an $i^{th}$ layer may be provided as an input to an $(i+1)^{th}$ layer, in which i is an integer equal to or greater than 1. Alternatively or additionally, an output of the $(i+1)^{th}$ layer may be propagated back to the $i^{th}$ layer according to a chain rule.

In some embodiments, in the preliminary model 1200, the input layer 1201 may be configured to receive an input of the preliminary model 1200 (e.g., the sample set as described in connection with operation 902 in FIG. 9). Each hidden layer 1202 may perform a specific function including, e.g., convolution, pooling, normalization, matrix multiplication, non-linear activation, or the like. The output layer 1203 may receive an input from the preceding layer and apply one or more transformations to the received input to generate a predicted result (e.g., a predicted T1 map or a predicted T1 value) of the preliminary model 1200.

For illustration purposes, the hidden layers 1202 may include a plurality of hidden layers 1202-1, 120s-2, ..., 1202-n. For example, the hidden layers 1202 may include a convolutional layer, a batch normalization layer, and a pooling layer, a fully connected layer, a loss layer, or the like, or any combination thereof. In some embodiments, an output of the convolutional layer may be processed by the batch normalization layer and the pooling layer, and fed into the convolutional layer. The convolutional layer may be used to extract and/or map feature information of the sample set. Exemplary feature information may include a low-level feature information (e.g., an edge feature, a textural feature), a high-level feature information, or a complicated feature. The batch normalization layer may be configured to receive and normalize an output of the convolutional layer (e.g., feature maps). The data normalization performed by the batch normalization layer may accelerate the convergence of the preliminary model and improve the stability of the preliminary model during the training process. For example, the batch normalization layer may force the distribution of an input value of an neuron in each layer of the preliminary model 1200 to a standard normal distribution with a mean value of 0 and a variance of 1; the batch normalization layer may make the input value of a non-linear function (that represents the preliminary model 1200) fall into an input sensitive area, so that a small change in the input value may cause a large change in a loss function to avoid the problem of gradient disappearance in low layers of the preliminary model 1200. A large gradient may result in a high convergence speed in the training of the preliminary model 1200. Each pooling layer may be used to sample the output of the batch normalization layer, so as to reduce the computational load of data processing and accelerate the data processing. The fully connected layer may be connected to the pooling layer. The fully connected layer may be used to perform refitting operations to reduce the loss of the feature information. The loss layer may be used to assess a loss function based on a correction result predicted by the preliminary model and the corresponding the reference T1 map (or the reference T1 value). The loss function may be used to measure a discrepancy between the predicated result (e.g., the predicted T1 map or the predicted T1 value) output by the updated preliminary model and the reference T1 map (or the reference T1 value). More descriptions for the loss function may be found elsewhere in the present disclosure. See, e.g., operation 904 in FIG. 9 and relevant descriptions thereof. It should be noted that the preliminary model 1200 described in FIG. 12 is merely provided for illustration purposes, and not intended to limit the scope of the present disclosure. A preliminary model having any other structures may be used for generating the trained model.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for magnetic resonance (MR) T1 mapping, comprising:
   at least one storage device including a set of instructions; and
   at least one processor in communication with the at least one storage device, wherein when executing the set of instructions, the at least one processor is directed to cause the system to perform operations including:
   obtaining at least three images of a subject acquired within an inversion recovery (IR) process, each image of the at least three images being acquired within a cardiac cycle during a breath-hold of the subject; and
   determining a T1 map of the subject based on the at least three images acquired within the IR process and a trained model, wherein the trained model is generated based on a machine learning algorithm.

2. The system of claim 1, wherein the operations further include:
   obtaining one or more processed images by processing one or more images of the at least three images; and
   determining the T1 map of the subject based on the one or more processed images and the trained model.

3. The system of claim 2, wherein the obtaining the one or more processed images by processing the one or more images of the at least three images includes:
   obtaining the one or more processed images by performing at least one of a motion correction algorithm or a phase correction algorithm on the one or more images of the at least three images.

4. The system of claim 1, wherein the trained model includes a fully connected neural network.

5. The system of claim 1, wherein the determining the T1 map of the subject based on the at least three images and the trained model includes:
   obtaining the T1 map of the subject by inputting the at least three images into the trained model, wherein the T1 map is an output of the trained model.

6. The system of claim 1, wherein the determining the T1 map of the subject based on the at least three images and the trained model includes:
   for an element location in the T1 map, determining a T1 value by inputting into the trained model at least three values of elements each of which is at a corresponding element location in one of the at least three images and an image acquisition time of each of the at least three images; and
   determining the T1 map based on a plurality of T1 values of a plurality of element locations in the T1 map.

7. The system of claim 6, wherein for an element location in the T1 map, the determining the T1 value includes:
   for each image of the at least three images,
   identifying an image acquisition time of the image, the image acquisition time being a time point at which the image is acquired during the IR process; and
   identifying a value of an element at each element location of the image.

8. The system of claim 1, wherein the trained model is determined based on a training process, the training process including:
   obtaining a plurality of sample sets, wherein each sample set includes a plurality of sample images, a plurality of sample image acquisition times each of which corresponds to one of the plurality of sample images, and a reference T1 map of the plurality of sample images; and obtaining the trained model by training a preliminary model based on the plurality of sample sets.

9. The system of claim 8, wherein the obtaining the plurality of sample sets includes:
for a sample set of the plurality of sample sets,
obtaining the plurality of sample images;
identifying a sample image acquisition time of each of the plurality of sample images; and
determining the reference T1 map of the plurality of sample images based on the plurality of sample images and the corresponding sample image acquisition times.

10. The system of claim 9, wherein the plurality of sample images of a sample set are acquired using a Modified Look-Locker Inversion Recovery (MOLLI) sequence.

11. The system of claim 9, wherein the reference T1 map of the plurality of sample images is determined according to a fitting algorithm.

12. A method for magnetic resonance (MR) T1 mapping, implemented on a computing device having one or more processors and one or more storage device, the method comprising:
obtaining, by the one or more processors, at least three images of a subject acquired within an inversion recovery (IR) process, each image of the at least three images being acquired within a cardiac cycle during a breath-hold of the subject; and
determining, by the one or more processors, a T1 map of the subject based on the at least three images acquired within the IR process and a trained model, wherein the trained model is generated based on a machine learning algorithm.

13. The method of claim 12, further comprising:
obtaining, by the one or more processors, one or more processed images by processing one or more images of the at least three images; and
determining, by the one or more processors, the T1 map of the subject based on the one or more processed images and the trained model.

14. The method of claim 13, wherein the obtaining the one or more processed images by processing the one or more images of the at least three images includes:
obtaining, by the one or more processors, the one or more processed images by performing at least one of a motion correction algorithm or a phase correction algorithm on the one or more images of the at least three images.

15. The method of claim 12, wherein the trained model includes a fully connected neural network.

16. The method of claim 12, wherein the determining the T1 map of the subject based on the at least three images and the trained model includes:

obtaining, by the one or more processors, the T1 map of the subject by inputting the at least three images into the trained model, wherein the T1 map is an output of the trained model.

17. The method of claim 12, the determining the T1 map of the subject based on the at least three images and the trained model includes:
for an element location in the T1 map, determining, by the one or more processors, a T1 value by inputting into the trained model at least three values of elements each of which is at a corresponding element location in one of the at least three images and an image acquisition time of each of the at least three images; and
determining, by the one or more processors, the T1 map based on a plurality of T1 values of a plurality of element locations in the T1 map.

18. The method of claim 17, wherein for an element location in the T1 map, the determining the T1 value includes:
for each image of the at least three images,
identifying, by the one or more processors, an image acquisition time of the image, the image acquisition time being a time point at which the image is acquired during the IR process; and
identifying, by the one or more processors, a value of an element at each element location of the image.

19. The method of claim 12, wherein the trained model is determined based on a training process, the training process including:
obtaining, by the one or more processors, a plurality of sample sets, wherein each sample set includes a plurality of sample images, a plurality of sample image acquisition times each of which corresponds to one of the plurality of sample images, and a reference T1 map of the plurality of sample images; and
obtaining, by the one or more processors, the trained model by training a preliminary model based on the plurality of sample sets.

20. A non-transitory computer readable medium, comprising executable instructions that, when executed by at least one processor, direct the at least one processor to perform a method, the method comprising:
obtaining, by the one or more processors, at least three images of a subject acquired within an inversion recovery (IR) process, each image of the at least three images being acquired within a cardiac cycle during a breath-hold of the subject; and
determining, by the one or more processors, a T1 map of the subject based on the at least three images acquired within the IR process and a trained model, wherein the trained model is generated based on a machine learning algorithm.

* * * * *